(12) United States Patent
Sato et al.

(10) Patent No.: US 9,988,411 B2
(45) Date of Patent: Jun. 5, 2018

(54) THIN-FILM-FORMING MATERIAL INCLUDING A MOLYBDENUM IMIDE COMPOUND

(71) Applicant: ADEKA CORPORATION, Tokyo (JP)

(72) Inventors: Hiroki Sato, Tokyo (JP); Junji Ueyama, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days. days.

(21) Appl. No.: 15/598,398

(22) Filed: May 18, 2017

(65) Prior Publication Data

US 2017/0253624 A1 Sep. 7, 2017

Related U.S. Application Data

(62) Division of application No. 14/421,154, filed as application No. PCT/JP2013/077889 on Oct. 15, 2013, now Pat. No. 9,695,207.

(30) Foreign Application Priority Data

Nov. 19, 2012 (JP) .................................. 2012-253276

(51) Int. Cl.
C07C 17/00 (2006.01)
C07F 11/00 (2006.01)
(Continued)

(52) U.S. Cl.
CPC .............. *C07F 17/00* (2013.01); *C07F 11/00* (2013.01); *C23C 16/18* (2013.01); *C23C 16/405* (2013.01);
(Continued)

(58) Field of Classification Search
CPC ... C23C 16/18; C23C 16/44; C23C 16/45525; C07C 17/00; C07F 11/00
(Continued)

(56) References Cited

U.S. PATENT DOCUMENTS 6,528,171 B1 3/2003 Endler
6,798,068 B2 9/2004 Oglesby
(Continued)

FOREIGN PATENT DOCUMENTS

CN 1458669 11/2003
JP 60-125372 7/1985
(Continued)

OTHER PUBLICATIONS

English translation of the Written Opinion of the International Search Authority dated Dec. 10, 2013 for PCT/JP2013/077889; 5 pages.*

(Continued)

*Primary Examiner* — Helene Klemanski
(74) *Attorney, Agent, or Firm* — Young & Thompson (57) ABSTRACT

In the method of the present invention for producing a thin film, including introducing, onto a substrate, a vapor that has been obtained by vaporizing a thin-film-forming material including a molybdenum imide compound represented by the following formula (I) and that includes the molybdenum imide compound; and then forming a thin film including molybdenum on the substrate by decomposing and/or chemically reacting the molybdenum imide compound.

(Continued)

(In the formula, $R^1$ though $R^{10}$ each represent a hydrogen atom or a linear or branched alkyl group having 1 to 5 carbon atoms, and $R^{11}$ represents a linear or branched alkyl group having 1 to 8 carbon atoms.)

16 Claims, 2 Drawing Sheets

(51) Int. Cl.
          *C23C 16/18*      (2006.01)
          *C23C 16/44*      (2006.01)
          *C23C 16/455*     (2006.01)
          *C07F 17/00*      (2006.01)
          *C23C 16/40*      (2006.01)

(52) U.S. Cl.
          CPC ........ *C23C 16/44* (2013.01); *C23C 16/45525* (2013.01)

(58) Field of Classification Search
          USPC ........................................................ 106/1.18
          See application file for complete search history.

(56) References Cited

U.S. PATENT DOCUMENTS

| | | | |
|---|---|---|---|
| 6,984,591 | B1 | 1/2006 | Buchanan |
| 7,036,801 | B2 | 5/2006 | Takamatsu |
| 7,323,581 | B1* | 1/2008 | Gardiner ............... C23C 16/18 106/1.25 |
| 8,795,771 | B2* | 8/2014 | Barry ..................... C23C 16/18 427/248.1 |
| 8,962,875 | B2 | 2/2015 | Norman et al. |
| 9,670,582 | B2* | 6/2017 | Barry ..................... C23C 16/18 |
| 9,695,207 | B2* | 7/2017 | Sato ......................... C07F 17/00 |
| 2003/0209201 | A1 | 11/2003 | Takamatsu |
| 2006/0068100 | A1 | 3/2006 | Machida et al. |
| 2006/0125129 | A1 | 6/2006 | Takamatsu |
| 2007/0232820 | A1* | 10/2007 | Meiere ................... C23C 16/18 556/59 |
| 2008/0081922 | A1 | 4/2008 | Meiere et al. |
| 2012/0077719 | A1 | 3/2012 | Bhalla |
| 2013/0011579 | A1 | 1/2013 | Norman et al. |
| 2013/0066082 | A1 | 3/2013 | Norman et al. |
| 2013/0157064 | A1 | 6/2013 | Perepezko |
| 2014/0141165 | A1* | 5/2014 | Sato ...................... C23C 16/405 427/255.31 |
| 2017/0253625 | A1* | 9/2017 | Sato ........................ C07F 17/00 |

FOREIGN PATENT DOCUMENTS

| | | |
|---|---|---|
| JP | 2003-342732 | 12/2003 |
| JP | 2006-097100 | 4/2006 |
| JP | 2006-131606 | 5/2006 |
| JP | 2012-246531 | 12/2012 |
| TW | I240011 | 9/2005 |
| TW | 201229286 | 7/2012 |
| WO | 2004048637 | 6/2004 |

OTHER PUBLICATIONS

International Search Report PCT/JP2013/077889 dated Dec. 10, 2013.
Malcolm L.H. Green, etc., Bis(η-cyclopentadienyl)imidomolybdenum Compounds, J. Chem. Soc. Dalton Trans., Jan. 21, 1995, No. 2, 155-162.
Jennifer C. Green, etc., Bis(η-cyclopentadienyl)-molybdenum and-tungsten Imido Complexes: X-Ray Structures of [Mo(η-C5h5)2(NBut)] and [Mo(η-C5H4Me)2(NBut)Me]I, J. Chem. Soc. Chem. Commun., Sep. 15, 1992, No. 18, 1361-1365.
Mohammad S. Askari and Xavier Ottenwaelder, Oxygen-atom transfer to a nucleophilic molybdenum complex, Dalton Trans, Mar. 14, 2010, vol. 39, No. 10, 2644-2650.
Green, Malcolm, et al., "Bis(n-cyclopentadienyl)imidomolybdenum Compounds". J. Chem. Soc. Dalton Trans. 1995, pp. 155-162.
Chen, Tianniu, et al., "Synthesis, characterization and X-ray structures of new molbdenum bis(imide) amide and silyl complexes". Inorganica Chimica Acta 345 (2003) 113-120.
Alias, Yatimah, et al., "Electrochemistry of molybdenum imides: cleavage of molybdenum-nitrogen triple bonds to release ammonia or amines". J. Chem. Soc., Dalton Trans., 1997, pp. 4807-4815.
Schmidt, Hennrik, et al., "Transport Properties of Monolayer MoS2 Grown by Chemical Vapor Deposition". Nano Lett. 2014, 14, 1909-1913.
Matsuura, Yuji, et al., "Infrared hollow glass waveguides fabricated by chemical vapor deposition". Optics Letters, vol. 20, No. 20, Oct. 15, 1995, pp. 2078-2080.
Potts, Stephen E. et al., "Tungsten imido complexes as precursors to tungsten carbonitride thin films", Dalton Trans., Sep. 9, 2008, No. 42, pp. 5730-5736. Abstract; pp. 5732-5733.
Singapore Search Report, 11201501107X, Jun. 24, 2016.
Republic of China Office Action dated Jul. 8, 2016; Application No. 201380043243.7.
"Recent Developments in Organometallic Chemistry"; by M.L.H. Green, Pure and Appl., Chem., vol. 67, No. 2, pp. 249-256; 1995.

\* cited by examiner

THIN-FILM-FORMING MATERIAL INCLUDING A MOLYBDENUM IMIDE COMPOUND

This application is a divisional of U.S. patent application Ser. No. 14/421,154, now U.S. Pat. No. 9,695,207.

TECHNICAL FIELD

The present invention relates to a method for producing a thin film containing molybdenum by using vapor formed by vaporizing a specific molybdenum imide compound, a thin film containing molybdenum and produced using the production method, and a material for thin film formation using the production method, and a novel molybdenum imide compound.

BACKGROUND ART

A thin film containing molybdenum can be used for an organic light emitting diode, a liquid crystal display, a plasma display panel, a field emission display, a thin film solar cell, a low-resistance ohmic as well as other electronic devices and semiconductor devices. The thin film is used mainly as a member of an electronic component such as a barrier film.

Examples of the method for producing the thin film mentioned above include a sputtering methods, an ion plating method, MOD methods such as a coating thermal decomposition method, and a sol-gel method, as well as chemical vapor deposition methods. Chemical vapor deposition (hereinafter sometimes referred to simply as CVD) methods including an ALD (Atomic Layer Deposition) method are optimal production processes because of their possession of many merits such as being excellent in composition controllability and step coverage, being suitable for mass-production, and being capable of hybrid integration.

Various molybdenum compounds have conventionally been known as molybdenum compounds to be used as a material for a CVD method. In, for example, patent literature 1 have been reported biscyclopentadienylmolybdenum dihydride, bismethylcyclopentadienylmolybdenum dihydride, bisethylcyclopentadienylmolybdenum dihydride, and bisisopropylcyclopentadienylmolybdenum dihydride. The compounds disclosed in patent literature 1, however, are high in melting point, low in vapor pressure, and problematic in that a large amount of residue is formed after thermal decomposition by heating, and therefore they were not compounds sufficiently satisfactory as a material for a CVD method.

In non-patent literature 1 has been disclosed biscyclopentadienylimidomolybdenum compounds. Non-patent literature 1, however, fails to disclose that biscyclopentadienylimidomolybdenum compounds are useful as a material for a CVD method.

CITATION LIST

Patent Literature

[Patent literature 1] US 2006/0068100 A1

Non Patent Literature

[Non-patent literature 1] J. CHEM. SOC. DALTON TRANS 1995, P. 155-162

SUMMARY OF INVENTION

Technical Problem

In the production of a thin film containing molybdenum by a CVD method, the molybdenum compounds having been proposed do not necessarily have sufficient characteristics. A thin film is formed by vaporizing a compound in CVD method or the like. A compound (precursor) suitable for material in such a method is required to have such properties as being high in thermal stability, being low in melting point, and being high in vapor pressure and therefore being easy to vaporize. Compounds which have heretofore been used as a molybdenum source were problematic in that they are high in melting point and low in vapor pressure and a large amount of residue remains after thermal decomposition by heating. If a large amount of residue thermally decomposed by heating was formed, there sometimes occurred problems such as that the quality of a desired thin film is deteriorated, that it becomes difficult to wash a pipe or a container, and that a pipe is plugged due to that the residue causes particles.

Solution to Problem

Through diligent effort, the present inventors have attained the present invention as a result of finding that a method for producing a thin film containing molybdenum by a CVD method using a specific molybdenum imide compound as a precursor can solve the above-described problems.

The present invention provides a method for producing a thin film, comprising introducing, onto a substrate, a vapor that has been obtained by vaporizing a thin-film-forming material comprising a molybdenum imide compound represented by the following formula (I) and that comprises the molybdenum imide compound, and then forming a thin film comprising molybdenum on the substrate by decomposing and/or chemically reacting the molybdenum imide compound. The present invention also provides a thin film containing molybdenum produced using the above-mentioned method for producing a thin film.

[Chemical Formula 1]

(I)

wherein $R^1$ though $R^{10}$ each represent a hydrogen atom or a linear or branched alkyl group having 1 to 5 carbon atoms, and $R^{11}$ represents a linear or branched alkyl group having 1 to 8 carbon atoms.

In addition, the present invention provides a material for thin film formation (thin-film-forming material) containing a molybdenum imide compound represented by the above formula (I).

Further, the present invention provides a novel molybdenum imide compound represented by the following formula (II).

[Chemical Formula 2]

wherein $R^{12}$ through $R^{21}$ each represent a hydrogen atom or a linear or branched alkyl group having 1 to 5 carbon atoms, $R^{22}$ and $R^{23}$ each represent a methyl group or an ethyl group, and $R^{24}$ represents a linear or branched alkyl group having 2 to 5 carbon atoms.

Effects of Invention

According to the present invention, it is possible to produce a high-quality thin film containing molybdenum in high mass productivity by using a thin-film-forming material containing a specific molybdenum imide compound. This compound is excellent in thermal stability, low in melting point and high in vapor pressure. Therefore, a property to transport a precursor is excellent in the production of a thin film containing molybdenum by a CVD method and the supply amount to a substrate can be controlled easily and stable supply can be attained when this compound is used to form a thin film.

DESCRIPTION OF EMBODIMENTS

In the following, preferred embodiments of the method for producing a thin film containing molybdenum of the present invention are described in detail.

In the above formula (I) of the present invention, examples of the linear or branched alkyl group having 1 to 5 carbon atoms represented by $R^1$ to $R^{10}$ include methyl, ethyl, propyl, isopropyl, butyl, secondary butyl, tertiary butyl, isobutyl, pentyl, secondary pentyl, tertiary pentyl, isopentyl, and neopentyl. Examples of the linear or branched alkyl group having 1 to 8 carbon atoms represented by $R^{11}$ include methyl, ethyl, propyl, isopropyl, butyl, secondary butyl, tertiary butyl, isobutyl, pentyl, secondary pentyl, tertiary pentyl, isopentyl, neopentyl, hexyl, 2-hexyl, 3-hexyl, cyclohexyl, 1-methylcyclohexyl, heptyl, 2-heptyl, 3-heptyl, isoheptyl, tertiary heptyl, n-octyl, isooctyl, tertiary octyl, and 2-ethylhexyl.

Specific examples of molybdenum imide compounds having such groups include Compounds Nos. 1 to 63 shown below. The present invention is not limited at all by the following exemplary compounds.

[Chemical Formula 3]

Compound No. 1

Compound No. 2

Compound No. 3

Compound No. 4

Compound No. 5

Compound No. 6

Compound No. 7

Compound No. 8

-continued

Compound No. 9

[Chemical Formula 4]

Compound No. 10

Compound No. 11

Compound No. 12

Compound No. 13

Compound No. 14

Compound No. 15

Compound No. 16

-continued

Compound No. 17

Compound No. 18

Compound No. 19

Compound No. 20

Compound No. 21

[Chemical Formula 5]

Compound No. 22

Compound No. 23

Compound No. 24

Compound No. 25

Compound No. 26

Compound No. 27

Compound No. 28

Compound No. 29

Compound No. 30

[Chemical Formula 6]

Compound No. 31

Compound No. 32

Compound No. 33

Compound No. 34

Compound No. 35

Compound No. 36

Compound No. 37

Compound No. 38

Compound No. 39

Compound No. 40

Compound No. 41

Compound No. 42

[Chemical Formula 7]

Compound No. 43

Compound No. 44

Compound No. 45

Compound No. 46

Compound No. 47

Compound No. 48

Compound No. 49

Compound No. 50

Compound No. 51

[Chemical Formula 8]

Compound No. 52

Compound No. 53

Compound No. 54

Compound No. 55

Compound No. 56

Compound No. 57

[Chemical Formula 9]

Compound No. 58

Compound No. 59

Compound No. 60

Compound No. 61

Compound No. 62

Compound No. 63

In the molybdenum imide compound to be used for the method for producing a thin film containing molybdenum of the present invention, $R^1$ through $R^{10}$ of the above formula (I) are each preferably one that allows the compound to have a low melting point and a high vapor pressure. Specifically, $R^1$ through $R^{10}$ are each preferably a hydrogen atom or a methyl group; a compound in which $R^1$ through $R^{10}$ are all hydrogen atoms and a compound in which one of $R^1$ to $R^5$ is a methyl group and one of $R^6$ to $R^{10}$ is a methyl group are particularly preferable because of their high vapor pressure. $R^{11}$ is preferably a tertiary alkyl group because a resulting melting point is low, and especially, a tertiary butyl group, a tertiary pentyl group, or a 1,1,3,3-tetramethylbutyl group is preferred. A compound in which $R^{11}$ is a tertiary pentyl group or a 1,1,3,3-tetramethylbutyl group is particularly preferable because its melting point is particularly low.

The thin-film-forming material of the present invention is one which allows the above-described molybdenum imide compound to serve as a precursor for the production of a thin film containing molybdenum and its form varies depending upon a process. The molybdenum imide compound represented by formula (I) is particularly useful as a material for a chemical vapor deposition method because of its physical properties.

When the thin-film-forming material of the present invention is a source material for chemical vapor deposition, the form thereof is chosen appropriately depending upon the techniques for a delivering and feeding method and others in the chemical vapor deposition process to be used.

The delivering and feeding method includes a vapor delivery method and a liquid delivery method. In the vapor delivery method, a source material for chemical vapor deposition is vaporized by heating and/or reducing pressure in a source container and the resulting vapor is introduced into the deposition reaction section optionally together with a carrier gas such as argon, nitrogen, and helium. In the liquid delivery method, a source material for chemical vapor deposition is delivered in a liquid or solution state to a vaporization chamber, vaporized by heating and/or reducing pressure in the vaporization chamber, and introduced into the deposition reaction section. In the vapor delivery method, the source material for chemical vapor deposition is the molybdenum imide compound represented by formula (I) itself, while in the liquid delivery method, the source material for chemical vapor deposition is the molybdenum imide compound represented by formula (I) itself or a solution containing the compound dissolved in an organic solvent.

Chemical vapor deposition processes for multi-component systems include a technique in which each component composing a source material for chemical vapor deposition is separately vaporized and fed (hereinafter may be also called "single source method") and a technique in which a mixed source obtained by pre-mixing a plurality of source components at a desired composition is vaporized and fed (hereinafter may be also called "cocktail source method"). In the cocktail source method, the source material for chemical vapor deposition is a mixture or mixed solution containing the molybdenum imide compound represented by formula (I) and other precursor(s).

As the organic solvent to be used for the source material for chemical vapor deposition, conventionally known organic solvent of general common knowledge can be used without any restriction. Examples of the organic solvent include ester acetates, such as ethyl acetate, butyl acetate, methoxyethyl acetate; ether alcohols, such as ethylene glycol monomethyl ether, ethylene glycol monoethyl ether, ethylene glycol monobutyl ether, and diethylene glycol monomethyl ether; ethers, such as tetrahydrofuran, tetrahydropyran, ethylene glycol dimethyl ether, diethylene glycol dimethyl ether, triethylene glycol dimethyl ether, dibutyl ethers, and dioxanes; ketones, such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons, such as hexane, cyclohexane, methylcyclohexane, dimethylcyclohexane, ethylcyclohexane, heptane, octane, toluene, and xylenes; hydrocarbons having a cyano group, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine, and lutidine; these are used individually or as a mixed solvent composed of two or more of them depending upon the solubility of a solute, the relation of the use temperature, the boiling point and the flashing point, etc. When using such an organic solvent, it is preferable to adjust the combined amount of the molybdenum imide compound represented by the above formula (I) and other precursors in the organic solvent to 0.01 to 2.0 mol/liter, especially to 0.05 to 1.0 mol/liter.

In the case of a material for multi-component chemical vapor deposition, any well-known common precursor used as a material for chemical vapor deposition may be used without any particular restriction as the other precursor(s) to be used together with the above-described molybdenum imide compound.

Examples of the other precursor(s) include compounds of silicon or metal with one or two or more organic coordination compounds selected from alcohol compounds, glycol compounds, β-diketone compounds, cyclopentadiene compounds, and organic amine compounds. Examples of the metal in a precursor includes lithium, sodium, potassium, magnesium, calcium, strontium, barium, titanium, zirconium, hafnium, vanadium, niobium, tantalum, molybdenum, manganese, iron, ruthenium, cobalt, rhodium, iridium, nickel, palladium, platinum, copper, silver, gold, zinc, aluminum, gallium, indium, germanium, tin, lead, antimony, bismuth, yttrium, lanthanum, cerium, praseodymium, neodymium, promethium, samarium, europium, gadolinium, terbium, dysprosium, holmium, erbium, thulium, and ytterbium.

Examples of alcohol compounds to be used as the organic ligand include alkyl alcohols such as methanol, ethanol, propanol, isopropanol, butanol, 2-butanol, isobutanol, tert-butanol, amyl alcohol, isoamyl alcohol, and tert-amyl alcohol; and ether alcohols such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-sec-butoxy-1,1-diethylethanol, and 3-methoxy-1,1-dimethylpropanol.

Examples of glycol compounds to be used as the organic ligand include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, and 2,4-hexanediol, 2,4-dimethyl-2,4-pentanediol.

Examples of the β-diketone compounds to be used as the organic ligand include alkyl-substituted β-diketones, such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione-2-methyl-6-ethyldecane-3,5-dione, and 2,2-dimethyl-6-ethyldecane-3,5-dione; fluorine-substituted alkyl-β-diketones, such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; ether-substituted β-diketones, such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

Examples of the cyclopentadiene compounds to be used as the organic ligand include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, dimethylcyclopentadiene, and tetramethylcyclopentadiene. Examples of the organic amine compounds to be used as the organic ligand include methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, and isopropylmethylamine.

In the case of the single source method, the aforementioned other precursor(s) is preferably a compound that exhibits a similar thermal and/or oxidative decomposition behavior. In the case of the cocktail source method, the aforementioned other precursor(s) is preferably a compound that not only exhibits a similar thermal and/or oxidative decomposition behavior but also fails to cause degradation due to chemical reactions during mixing.

In the material for the chemical vapor deposition of the present invention, there should be minimized contamination with substances other than components thereof including metal element impurities, halogen impurities such as chlorine impurities, and organic impurities. The content of the metal element impurities is preferably 100 ppb or less, more preferably 10 ppb or less for each element. The content of the metal element impurities is preferably 1 ppm or less, more preferably 100 ppb or less in total. Especially, when using as a gate dielectric layer, a gate layer, or a barrier layer of LSI, it is necessary to reduce the content of alkali metal elements, alkaline earth metal elements, and same group elements (chromium or tungsten) which affect the electric properties of an electric thin film to be obtained. The amount of the halogen impurities is preferably 100 ppm or less, more preferably 10 ppm or less, and even more preferably 1 ppm or less. The total content of organic impurities is preferably not more than 500 ppm, more preferably not more than 50 ppm, and even more preferably not more than 10 ppm. Since water causes particle generation in a chemical vapor deposition source or particle generation during thin film formation, it is recommended for each of the metal compound, the organic solvent, and the nucleophilic reagent to remove water as much as possible prior to use in order to reduce the water content thereof. In each of the metal compound, the organic solvent, and the nucleophilic reagent, the water content is preferably not more than 10 ppm and more preferably not more than 1 ppm.

In the material for chemical vapor deposition of the present invention, it is preferable to minimize contamination with particles as much as possible in order to reduce or prevent the particle pollution of a thin film to be formed. Specifically, in particle measurement with a light-scattering submerged particle detector in a liquid phase, the number of particles larger than 0.3 µm is preferably 100 or less in 1 ml of the liquid phase, more preferably the number of particles larger than 0.2 µm is 1000 or less in 1 ml of the liquid phase, and even more preferably the number of particles larger than 0.2 µm is 100 or less in 1 ml of the liquid phase.

The method for producing a thin film containing molybdenum of the present invention is one using a chemical vapor deposition method. In the method, a gas containing a molybdenum imide compound obtained by vaporizing a molybdenum imide compound represented by formula (I), a gas obtained by vaporizing other precursor(s) to be used as necessary, and a reactive gas are introduced onto a substrate, and then the molybdenum imide compound and the other precursor(s) to be used as necessary are decomposed and/or allowed to react on the substrate to grow and deposit a desired thin film on the substrate. A delivering and feeding method, a deposition method, production conditions, a production apparatus, and so on for a material are not particularly limited and well-known common conditions, methods, and so on can be used.

Examples of the reactive gas optionally used include oxidative ones, such as oxygen, ozone, nitrogen dioxide, nitrogen monoxide, water vapor, hydrogen peroxide, formic acid, acetic acid, and acetic anhydride; reductive ones, such as hydrogen; and nitriding agents including organic amine compounds such as monoalkylamines, dialkylamines, trialkylamines, and alkylenediamines, hydrazine, and ammonia. These may be used individually or two or more of them may be used in combination.

Examples of the above-mentioned delivering and feeding method include a vapor delivery method, a liquid delivery method, a single source method, and a cocktail source, which are described above.

The aforementioned deposition methods include the thermal CVD method in which a molybdenum imide compound (and another precursor gas) and a reactive gas are reacted only by heat to deposit a thin film, a plasma CVD method in which heat and plasma are used, a light CVD method in which heat and light are used, a light and plasma CVD method in which heat, light and plasma are used, and an ALD method in which the deposition reaction in a CVD method is separated into elementary steps and deposition is carried out step by step in a molecular level.

Examples of the material of the substrate include silicon; ceramics, such as silicon nitride, titanium nitride, tantalum nitride, titanium oxide, titanium nitride, ruthenium oxide, zirconium oxide, hafnium oxide, and lanthanum oxide; glass; and metals, such as metallic ruthenium. Examples of the shape of the substrate include a plate-like shape, a spherical shape, a fibrous shape, and a scale-like shape, and the surface of the substrate may be a plane or alternatively may be of a three-dimensional structure such as a trench structure.

Examples of the production conditions include a reaction temperature (a substrate temperature), a reaction pressure, and a deposition rate. The reaction temperature is preferably 100° C. or higher, at which the molybdenum imide compound is sufficiently reactive, and more preferably 100 to 300° C. The reaction pressure is preferably 0.01 to 300 Pa in the case of a thermal CVD method, a light CVD method, and a plasma CVD method. The deposition rate is controllable with conditions for supplying materials (vaporization temperature, vaporization pressure), a reaction temperature, and a reaction pressure. Since an excessively high deposition rate may lead to deterioration in properties of a resulting thin film and an excessively low deposition rate may cause a problem in productivity, the deposition rate is preferably 0.2 to 40.0 nm/min and more preferably 4.0 to 25.0 nm/min. In the case of an ALD method, it is controlled by the number of cycles so that a desired thickness may be obtained.

For example, when forming a molybdenum oxide thin film by an ALD method, there is performed a material introduction step of vaporizing a thin-film-forming material by the above-described delivering and feeding method to form a vapor and introducing the vapor onto a substrate (specifically, into a deposition reaction section where the substrate is placed). Subsequently, a precursor thin film is formed on the substrate from the molybdenum imide compound introduced into the deposition reaction section (precursor thin film formation step). At this time, heat may be added by heating the substrate or heating the deposition reaction section. The precursor thin film formed in this step is a molybdenum imide thin film or a thin film formed through decomposition and/or reaction of part of the molybdenum imide compound and has a composition different from the target molybdenum thin film. The temperature at which this step is carried out is preferably room temperature to 500° C., more preferably 100 to 300° C.

Subsequently, unreacted molybdenum imide compound gas and by-produced gas are exhausted from the deposition reaction section (exhaustion step). Although the unreacted molybdenum imide compound gas and the by-produced gas are ideally exhausted completely from the deposition reaction section, complete exhaustion is not always required. Examples of the method of exhaustion include a method in which the system is purged with an inert gas such as helium and argon, a method in which exhaustion is achieved by reducing the pressure in the system, and a method in which these are combined. The magnitude of reduced pressure in reducing the pressure is preferably 0.01 to 300 Pa, more preferably 0.1 to 100 Pa.

Subsequently, an oxidative gas is introduced into the deposition reaction section, and then by the action of the oxidative gas or the oxidative gas and heat, a molybdenum oxide thin film is formed on the precursor thin film formed in the preceding precursor thin film formation step (molybdenum oxide thin film formation step). The temperature at which heat is applied in this step is preferably room temperature to 500° C., more preferably 100 to 300° C. The molybdenum imide compound represented by formula (I) has a good reactivity with an oxidative gas and can afford a molybdenum oxide thin film.

A cycle of thin film deposition composed of a series of operations consisting of the above-described material introduction step, precursor thin film formation step, exhaustion step, and molybdenum oxide thin film formation step may be repeated a plurality of times until a thin film having a necessary thickness is obtained. In this case, preferably, after the execution of one cycle, unreacted molybdenum imide compound gas, oxidative gas, and by-produced gas are exhausted from the deposition reaction section in the same way as the above-described exhaustion step, and then the next cycle is conducted.

In the formation of a molybdenum oxide thin film by the ALD method, energy, such as plasma, light, and voltage, may be applied. The time when such energy is applied is not particularly limited; this time may be during the introduction of the molybdenum imide compound gas in the material introduction step, at the time of heating in the precursor thin film formation step or the molybdenum oxide thin film formation step, during the exhaustion of the system in the exhaustion step, or during the introduction of oxidative gas in the molybdenum oxide thin film formation step, and it also may be between the steps described above.

In the thin film formation method of the present invention, there may be carried out an annealing treatment under an inert atmosphere, an oxidative gas or reducing gas atmosphere in order to attain better film properties after the thin film deposition. When steps are required to be embedded, a reflow step may be provided. The temperature in this case is preferably 400 to 1200° C., particularly preferably 500 to 800° C.

Figure 1:
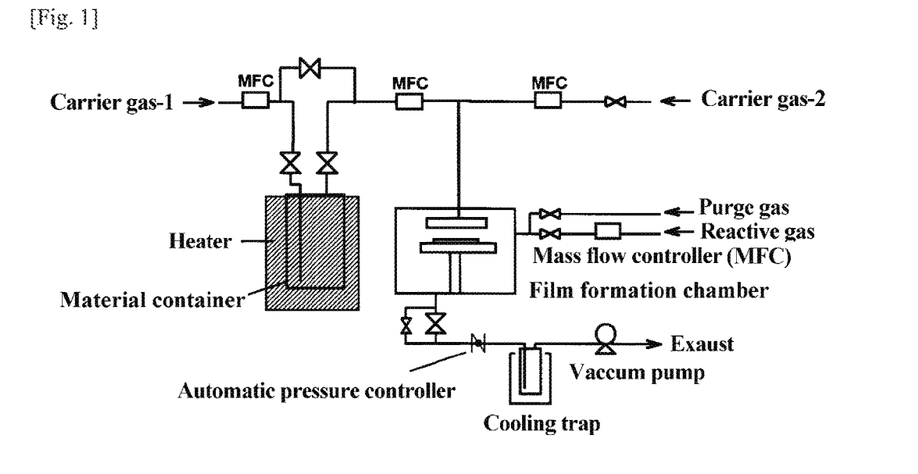
FIG. 1 is a schematic diagram illustrating an exemplary chemical vapor deposition apparatus to be used for the method for producing a thin film containing molybdenum according to the present invention.
Figure 2:
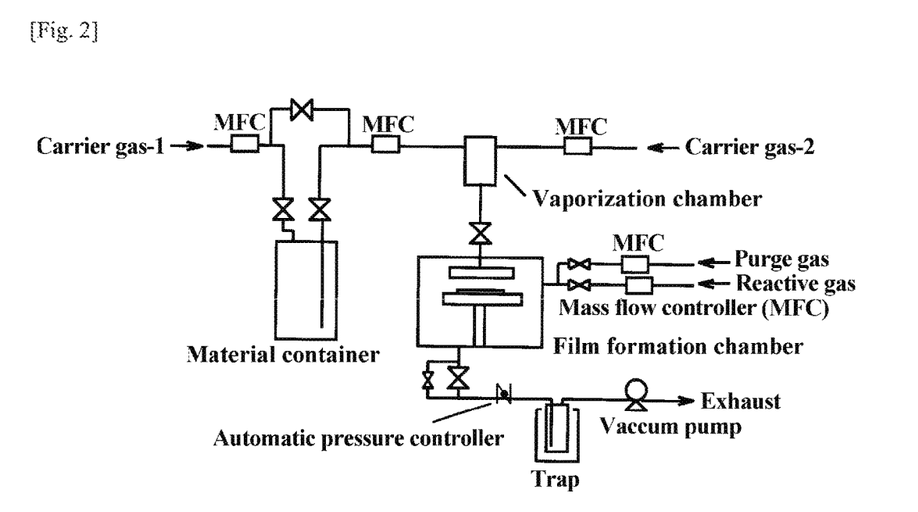
FIG. 2 is a schematic diagram illustrating another exemplary chemical vapor deposition apparatus to be used for the method for producing a thin film containing molybdenum according to the present invention.
Figure 3:
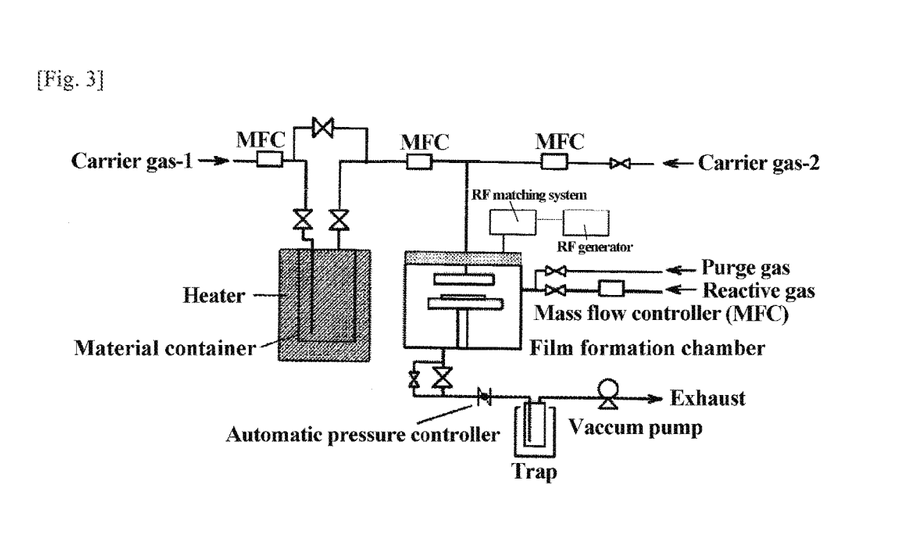
FIG. 3 is a schematic diagram illustrating another exemplary chemical vapor deposition apparatus to be used for the method for producing a thin film containing molybdenum according to the present invention.
Figure 4:
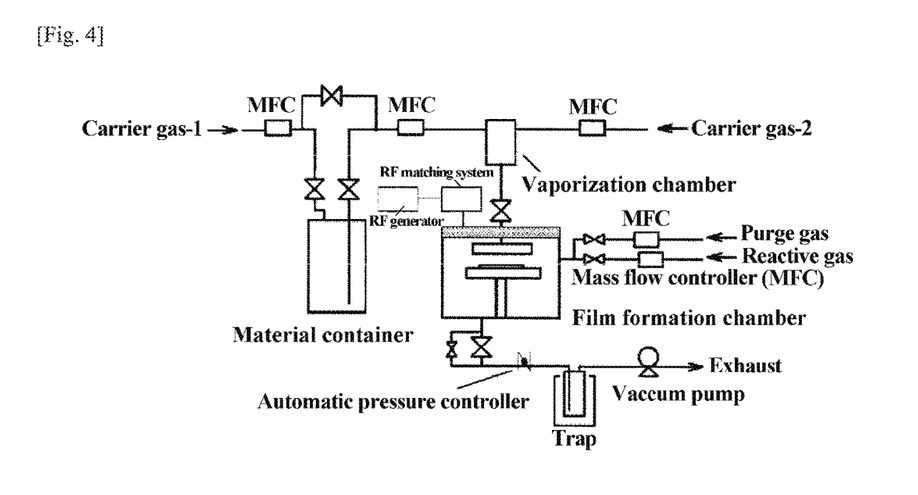
FIG. 4 is a schematic diagram illustrating another exemplary chemical vapor deposition apparatus to be used for the method for producing a thin film containing molybdenum according to the present invention.

The apparatus to be used for producing the thin film using the thin-film-forming material of the present invention may be a conventional apparatus for chemical vapor deposition. Examples of a specific apparatus include an apparatus capable of carrying out the supply of a precursor by bubbling as depicted in FIG. 1 and an apparatus having a vaporization chamber as depicted in FIG. 2. Other examples include apparatuses capable of performing plasma treatment to a reactive gas as depicted in FIG. 3 and FIG. 4. Not only single wafer type apparatuses such as those depicted in FIGS. 1, 2, 3 and 4 but also apparatuses capable of treating a multiple of wafers at the same time using a batch furnace can be used. The above-mentioned deposition reaction section corresponds to the film formation chambers in FIGS. 1 to 4.

Examples of the thin film containing molybdenum produced using the material for chemical vapor deposition of the present invention include metallic molybdenum, molybdenum nitride, molybdenum dioxide, molybdenum trioxide, molybdenum-sodium mixed oxides, molybdenum-calcium mixed oxides, molybdenum-bismuth mixed oxides, molybdenum-niobium mixed oxides, molybdenum-zinc mixed oxides, molybdenum-silicon mixed oxides, and molybdenum-cerium mixed oxides. Examples of their applications include electronic component members such as an electrode and a barrier film, a catalyst, a material for a catalyst, a material for metal, a metal surface treating agent, a ceramic additive, a sintered metal additive, a flame retardant, a smoke suppressing agent, a material for an antifreezing solution, a color former for an inorganic pigment, a basic dye mordant, a material for a rust inhibitor, a trace fertilizer for agriculture, and an auxiliary material for ceramic industries.

The molybdenum imide compound represented by the above formula (I) of the present invention is not limited by the process of the preparation thereof and can be prepared by using well-known reactions. Well-known common synthetic methods of metal imide compounds using the corresponding imide compounds can be applied as a production method. For example, there is mentioned a method in which triphenylphosphine is, as necessary, made to react with an alkylimidated oxomolybdenum halide compound having a corresponding structure, and then a cyclopentadiene compound derivative having a corresponding structure is further made to react.

The novel molybdenum imide compound of the present invention is a compound represented by the above formula (II). Since the novel molybdenum imide compound of the present invention is low in melting point and high in vapor pressure, it is a particularly suitable compound as a precursor for a thin film production method having a vaporization step of a CVD method or the like.

In the above formula (II) of the present invention, $R^{12}$ to $R^{21}$ each represent a hydrogen atom or a linear or branched alkyl group having 1 to 5 carbon atoms. Examples of the linear or branched alkyl group having 1 to 5 carbon atoms include methyl, ethyl, propyl, isopropyl, butyl, secondary butyl, tertiary butyl, isobutyl, pentyl, secondary pentyl, tertiary pentyl, isopentyl, and neopentyl. $R^{12}$ through $R^{21}$ of the above formula (II) are each preferably one that allows the compound to have a low melting point and a high vapor pressure, and specifically, $R^{12}$ through $R^{21}$ are each preferably a hydrogen atom or a methyl group; a compound in which $R^{12}$ through $R^{21}$ are all hydrogen atoms and a compound in which one of $R^{12}$ to $R^{16}$ is a methyl group and one of $R^{17}$ to $R^{21}$ is a methyl group are particularly preferable because of their high vapor pressure. In the above formula (II) of the present invention, $R^{22}$ and $R^{23}$ each represent a methyl group or an ethyl group. Although the carbon to which $R^{22}$ and $R^{23}$ are attached may be optically active depending upon the groups chosen, the compound is not distinguished by whether it is an R-isomer or an S-isomer; either form is available and a mixture of an R-isomer and an S-isomer is also available. A racemic mixture is lower in production cost. The case where at least one of $R^{22}$ and $R^{23}$ is a methyl group is preferable because a high vapor pressure is afforded. Examples of the linear or branched alkyl group having 2 to 5 carbon atoms represented by $R^{24}$ in the above formula (II) of the present invention include ethyl, propyl, isopropyl, butyl, secondary butyl, tertiary butyl, isobutyl, pentyl, secondary pentyl, tertiary pentyl, isopentyl, and neopentyl. Compounds of the above formula (II) of the present invention in which $R^{12}$ to $R^{21}$ are hydrogen atoms, $R^{22}$ and $R^{23}$ are methyl groups, and $R^{24}$ is ethyl or neopentyl and compounds in which one of $R^{12}$ to $R^{16}$ is a methyl group, one of $R^{17}$ to $R^{21}$ is a methyl group, $R^{22}$ and $R^{23}$ are methyl groups, and $R^{24}$ is ethyl or neopentyl are preferable because they are low in melting point and high in vapor pressure; especially, a compound in which $R^{12}$ to $R^{21}$ are hydrogen atoms, $R^{22}$ and $R^{23}$ are methyl groups, and $R^{24}$ is neopentyl and a compound in which one of $R^{12}$ to $R^{16}$ is a methyl group, one of $R^{17}$ to $R^{21}$ is a methyl group, $R^{22}$ and $R^{23}$ are methyl groups, and $R^{24}$ is ethyl or neopentyl are particularly preferable because they are very low in melting point.

Specific examples of the compound represented by the above formula (II) of the present invention include compound Nos. 9, 19, 30, and 40 provided above. The present invention is not limited at all by the exemplary compounds disclosed above.

The molybdenum imide compound represented by the above formula (II) of the present invention is not limited by the process of the preparation thereof and can be prepared by using well-known reactions. Well-known common synthetic methods of metal imide compounds using the corresponding imide compounds can be applied as a production method. For example, there is mentioned a method in which triphenylphosphine is, as necessary, made to react with an alkylimidated oxomolybdenum halide compound having a corresponding structure, and then a cyclopentadiene compound derivative having a corresponding structure is further made to react.

EXAMPLES

The present invention is described in more detail below with reference to production examples, evaluation examples, and examples. The present invention, however, is not limited thereto.

[Production Example 1] Synthesis and Analysis of Compound No. 6

Under dry argon gas atmosphere, 76.9 g (0.08 mol) of a 26.9 mass % triphenylphosphine solution in tetrahydrofuran was added to 81.4 g (0.07 mol) of a 30.7 mass % tert-butylimido-dichlorooxomolybdenum in tetrahydrofuran in a 500-mL reaction flask and was allowed to react at room temperature for 16 hours. To this molybdenum solution was added dropwise a solution of sodium cyclopentadienyl (0.18 mol) in tetrahydrofuran, and then reflux was carried out for 6 hours. The solvent was concentrated by evaporation under reduced pressure, followed by addition of hexane, reflux for 3 hours, and lowering of temperature to room temperature, and then filtration was carried out with a G4 ball filter. This filtrate was concentrated by evaporation under reduced pressure and then sublimed at 120° C. and 40 Pa, affording a crude product. A solution of the crude product in hexane was then cooled to −30° C. to recrystallize, so that compound No. 6 (dark reddish violet solid) was obtained. The following analyses were conducted for the resulting dark reddish violet solid.
(Analytical Values)
  (1) Elemental analysis (Metal analysis: ICP-AES)
  Molybdenum: 31.97% by mass (theoretical value: 32.28%), C: 56.2% by mass, H: 6.7% by mass, N: 4.9% by mass (theoretical values: C: 56.6%, H: 6.4%, N: 4.7%)
  (2) $^1$H-NMR (solvent: deuterated benzene) (chemical shift: multiplicity: the number of H)
  (1.04:s:9) (5.12:s:10)
  (3) TG-DTA
  (Ar 100 ml/min, 10° C./min temperature elevation, the amount of sample: 9.177 mg)
  50 mass % loss temperature: 219° C.

[Production Example 2] Synthesis and Analysis of Compound No. 27

Under dry argon gas atmosphere, 0.03 mol of triphenylphosphine was added to 138.83 g (0.15 mol) of a 36.2 mass % solution of tert-butylimido-dichlorooxomolybdenum in tetrahydrofuran in a 500-mL reaction flask and was allowed to react at room temperature for 16 hours. To this molybdenum solution was added dropwise a solution of sodium methylcyclopentadienyl (0.32 mol) in tetrahydrofuran, and then reflux was carried out for 6 hours. The solvent was concentrated by evaporation under reduced pressure, followed by addition of hexane, reflux for 15 minutes, lowering of temperature to room temperature, and addition of 11.5 g of cerite, and then filtration was carried out with a 0.5-μm filter. The filtrate was concentrated by evaporation under reduced pressure and then a fraction with a column top temperature of 116 to 119° C. at 40 Pa was taken by distillation under reduced pressure to obtain Compound No. 27 (dark reddish violet solid). The following analyses were conducted for the resulting dark reddish violet solid.
(Analytical Values)
  (1) Elemental analysis (Metal analysis: ICP-AES)
  Molybdenum: 38.8% by mass (theoretical value: 29.49%), C: 58.6% by mass, H: 6.7% by mass, N: 4.5% by mass (theoretical values: C: 59.1%, H: 7.1%, N: 4.3%)
  (2) $^1$H-NMR (solvent: deuterated benzene) (chemical shift: multiplicity: the number of H)
  (1.10:s:9) (1.91:s:6) (4.82:t:4) (5.23:t:4)
  (3) TG-DTA
  (Ar 100 ml/min, 10° C./min temperature elevation, the amount of sample: 10.314 mg)
  50 mass % loss temperature: 222° C.

[Example 1] Synthesis and Analysis of Compound No. 19

Under dry argon gas atmosphere, 0.03 mol of triphenylphosphine was added to 158.1 g (0.15 mol) of a 38.0 mass % solution of 1,1,3,3-tetramethylbutylimido-dichlorooxomolybdenum in tetrahydrofuran in a 500-mL reaction flask and was allowed to react at room temperature for 20 hours. To this molybdenum solution was added dropwise a solution of sodium cyclopentadienyl (0.32 mol) in tetrahydrofuran, and then reflux was carried out for 6 hours. The solvent was concentrated by evaporation under reduced pressure and then hexane and cerite were added, followed by filtration with a 0.5-μm filter. The filtrate was concentrated by evaporation under reduced pressure and then a fraction with a column top temperature of 136° C. at 45 Pa was taken by distillation under reduced pressure to obtain Compound No. 19 (dark reddish violet liquid). The following analyses were conducted for the resulting dark reddish violet liquid.
(Analytical Values)
  (1) Elemental analysis (Metal analysis: ICP-AES)
  Molybdenum: 26.1% by mass (theoretical value: 27.15%), C: 60.7% by mass, H: 7.2% by mass, N: 3.8% by mass (theoretical values: C: 61.2%, H: 7.7%, N: 4.0%)
  (2) $^1$H-NMR (solvent: deuterated benzene) (chemical shift: multiplicity: the number of H)
  (1.02:s:9) (1.10:s:6) (1.39:s:2) (5.12:s:10)
  (3) TG-DTA
  (Ar 100 ml/min, 10° C./min temperature elevation, the amount of sample: 10.411 mg)
  50 mass % loss temperature: 251° C.

[Example 2] Synthesis and Analysis of Compound No. 30

Under dry argon gas atmosphere, a solution of sodium methylcyclopentadienyl (0.18 mol) in tetrahydrofuran was added dropwise to 75.76 g (0.08 mol) of a 39.6 mass % tert-amylimodo-dichlorooxomolybdenum in tetrahydrofuran in a 500-mL reaction flask, and then reflux was carried out for 6 hours. The solvent was concentrated by evaporation under reduced pressure, followed by addition of hexane, reflux for 2 hours, and lowering of temperature to room temperature, and then filtration was carried out with a 0.5-μm filter. The filtrate was concentrated by evaporation under reduced pressure and then a fraction with a column top temperature of 118 to 121° C. at 40 Pa was taken by distillation under reduced pressure to obtain Compound No. 30 (dark reddish violet liquid). The following analyses were conducted for the resulting dark reddish violet liquid.
(Analytical Values)
  (1) Elemental analysis (Metal analysis: ICP-AES)
  Molybdenum: 28.7% by mass (theoretical value: 28.27%), C: 60.7% by mass, H: 7.2% by mass, N: 4.3% by mass (theoretical values: C: 60.2%, H: 7.4%, N: 4.1%)
  (2) $^1$H-NMR (solvent: deuterated benzene) (chemical shift: multiplicity: the number of H)
  (0.93:t:3) (1.03:s:6) (1.32:q:2) (1.92:s:6) (4.76:t:4) (5.25:t:4)
  (3) TG-DTA
  (Ar 100 ml/min, 10° C./min temperature elevation, the amount of sample: 10.932 mg)
  50 mass % loss temperature: 236° C.

[Example 3] Synthesis and Analysis of Compound No. 40

Under dry argon gas atmosphere, 0.062 mol of 1,1,3,3-tetramethylbutylimido-dichlorooxomolybdenum, 0.625 mol of tetrahydrofuran, and 0.01 mol of triphenylphosphine were added to a 500-mL reaction flask and were allowed to react at room temperature for 20 hours. To this molybdenum solution was added dropwise a solution of sodium methylcyclopentadienyl (0.131 mol) in tetrahydrofuran, and then reflux was carried out for 6 hours. The solvent was concentrated by evaporation under reduced pressure and then hexane and cerite were added, followed by filtration with a 0.5-μm filter. The filtrate was concentrated by evaporation under reduced pressure and then a fraction with a column top temperature of 142° C. at 33 Pa was taken by distillation under reduced pressure to obtain Compound No. 40 (dark reddish violet liquid). The following analyses were conducted for the resulting dark reddish violet liquid.
(Analytical Values)
  (1) Elemental analysis (Metal analysis: ICP-AES)
  Molybdenum: 24.7% by mass (theoretical value: 25.154%), C: 62.5% by mass, H: 8.4% by mass, N: 3.8% by mass (theoretical values: C: 63.0%, H: 8.2%, N: 3.7%)
  (2) $^1$H-NMR (solvent: deuterated benzene) (chemical shift: multiplicity: the number of H)
  (1.03:s:9) (1.15:s:6) (1.46:s:2) (1.93:s:6) (4.75:t:4) (5.29:t:4)
  (3) TG-DTA
  (Ar 100 ml/min, 10° C./min temperature elevation, the amount of sample: 11.349 mg)
  50 mass % loss temperature: 259° C.

[Evaluation Example 1] Evaluation of Physical Properties of Molybdenum Compound

For the compound Nos. 6, 19, 27, 30, 40 and the comparative compound 1 shown below, the state under normal pressure at 20° C. of each compound was observed visually. For solid compounds, a melting point was measured with a DSC analyzer. Moreover, a temperature at 50 mass % by weight loss (hereinafter sometimes abbreviated as 50% T) and a mass % lost on heating to 400° C. (hereinafter sometimes abbreviated as 400 wt) were measured by measuring a TG-DTA (normal pressure, Ar flow rate: 100 ml/min, temperature ramp-up: 10° C./min). Results are shown in Table 1.

[Chemical Formula 10]

Comparative compound 1

TABLE 1

| | Compound | State | Melting point/ °C. | 50% T/ °C. | 400 wt/ % by mass |
|---|---|---|---|---|---|
| Comparative Example 1 | Comparative Compound 1 | Solid | 180[×1] | 210 | 59.2 |
| Evaluation Example 1-1 | Compound No. 6 | Solid | 145 | 220 | 99.0< |
| Evaluation Example 1-2 | Compound No. 27 | Solid | 30 | 220 | 97.0< |
| Evaluation Example 1-3 | Compound No. 30 | Liquid | <20 | 235 | 93.0< |
| Evaluation Example 1-4 | Compound No. 19 | Liquid | <20 | 250 | 99.2< |
| Evaluation Example 1-5 | Compound No. 40 | Liquid | <20 | 255 | 83.1< |

*[1]The compound did not become liquid but decomposed while remaining solid.

According to the results shown in Table 1, Evaluation Examples 1-1 to 1-5 resulted in melting points greatly lower than that of Comparative Example 1, which showed that especially Evaluation Examples 1-3 to 1-5 afforded compounds which are liquid at temperatures lower than 20° C. Since a compound with a low melting point easily allows a material to be supplied in a liquid state stably, it is advantageous as a material for a chemical vapor deposition method. In comparison of Evaluation Examples 1-1 to 1-5 with Comparative Example 1 with respect to 50% T, it was shown that there was no large difference and they were almost equivalent in vapor pressure. It was found that heating to 400° C. caused thermal decomposition and allowed a large amount of residue to be formed in Comparative Example 1, whereas there remained a very small amount of residue formed by thermal decomposition on heating to 400° C. in Evaluation Examples 1-1 to 1-5.

[Example 4] Production of Molybdenum Oxide Thin Film

A molybdenum oxide thin film was produced on a silicon wafer with an apparatus depicted in FIG. 1 by an ALD method under the conditions described below using compound No. 19 as a material for chemical vapor deposition. When thickness measurement by an X-ray reflectance method and examination of the thin film composition by an X-ray photoelectron spectroscopy were carried out for the resulting thin film, the thickness was 1.5 nm, the film composition was molybdenum oxide (MoOx:x=2 to 3), and the carbon content was less than 0.1 atom %, which is a minimum limit of detection. The film thickness obtained per cycle was 0.03 nm.

(Conditions)
Reaction temperature (substrate temperature): 280° C., reactive gas: ozone gas
(Step)
A cycle composed of a series of steps (1) to (4) described below were repeated 50 times.
(1) A vapor of a material for chemical vapor deposition vaporized under conditions defined by a material container temperature of 90° C. and a material container pressure of 70 Pa is introduced and deposited for 10 seconds under a system pressure of 100 Pa.
(2) An unreacted material is removed by a 15-seconds argon purge.
(3) A reactive gas is introduced and made to react for 10 seconds under a system pressure of 100 Pa.
(4) An unreacted material is removed by a 15-seconds argon purge.

The invention claimed is:
1. A thin-film-forming material comprising a molybdenum imide compound represented by the following formula (I), used in a method for producing a thin film, the method comprising:
introducing, onto a substrate, a vapor that has been obtained by vaporizing the thin-film-forming material and that comprises the molybdenum imide compound; and
forming a thin film comprising molybdenum on the substrate by decomposing and/or chemically reacting the molybdenum imide compound

(I)

wherein $R^1$ through $R^{10}$ each represent a hydrogen atom or a linear or branched alkyl group having 1 to 5 carbon atoms, and $R^{11}$ represents a branched alkyl group having 4 to 8 carbon atoms.
2. The thin film material according to claim 1, wherein the thin film material is liquid at a temperature lower than 20° C.
3. The thin film material according to claim 1, wherein in the formula (I) of the linear or branched alkyl group having 1 to 5 carbon atoms represented by $R^1$ to $R^{10}$ is selected from the group consisting of methyl, ethyl, propyl, isopropyl, butyl, secondary butyl, tertiary butyl, isobutyl, pentyl, secondary pentyl, tertiary pentyl, isopentyl and neopentyl.
4. The thin film material according to claim 1, wherein in the formula (I) of the branched alkyl group having 4 to 8 carbon atoms represented by $R^{11}$ is selected from the group consisting of secondary butyl, tertiary butyl, isobutyl, secondary pentyl, tertiary pentyl, isopentyl, neopentyl, isoheptyl, tertiary heptyl, isooctyl, tertiary octyl and 2-ethylhexyl.
5. The thin film material according to claim 1, wherein in the formula (I), $R^1$ to $R^{10}$ is hydrogen or methyl.
6. The thin film material according to claim 1, wherein in the formula (I), $R^{11}$ is a tertiary alkyl group.
7. The thin film material according to claim 1, wherein in the formula (I), $R^{11}$ is tertiary butyl group, a tertiary pentyl group, or a 1,1,3,3-tetramethylbutyl group.

8. The thin film material according to claim 1, wherein in the formula (I), $R^{11}$ is a tertiary pentyl group or a 1,1,3,3-tetramethylbutyl group.

9. The thin film material according to claim 1, wherein the thin film material further comprises an organic solvent.

10. The thin film material according to claim 9, wherein the organic solvent is at least one selected from the group consisting of ethyl acetate, butyl acetate, methoxyethyl acetate, ethylene glycol monomethyl ether, ethylene glycol monoethyl ether, ethylene glycol monobutyl ether, diethylene glycol monomethyl ether, tetrahydrofuran, tetrahydropyran, ethylene glycol dimethyl ether, diethylene glycol dimethyl ether, triethylene glycol dimethyl ether, dibutyl ethers, dioxanes, methyl butyl ketone, methyl isobutyl ketone, ethyl butyl ketone, dipropyl ketone, diisobutyl ketone, methyl amyl ketone, cyclohexanone, methylcyclohexanone, hexane, cyclohexane, methylcyclohexane, dimethylcyclohexane, ethylcyclohexane, heptane, octane, toluene, xylenes, 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene, pyridine, and lutidine.

11. The thin film material according to claim 9, wherein an amount of the molybdenum imide compound represented by the formula (I) is 0.01 to 2.0 mol/liter.

12. The thin film material according to claim 9, wherein an amount of the molybdenum imide compound represented by the formula (I) is 0.05 to 1.0 mol/liter.

13. A thin-film-forming material comprising a molybdenum imide compound represented by the following formula (I), used in a method for producing a thin film, the method comprising:

introducing, onto a substrate, a vapor that has been obtained by vaporizing the thin-film-forming material and that comprises the molybdenum imide compound; and forming a thin film comprising molybdenum on the substrate by decomposing and/or chemically reacting the molybdenum imide compound (1)

wherein $R^1$ through $R^{10}$ each represent a hydrogen atom or a linear or branched alkyl group having 1 to 5 carbon atoms, and $R^{11}$ represents a branched alkyl group having 4 to 8 carbon atoms, and the thin film material is liquid at a temperature lower than 20° C.

14. The thin film material according to claim 13, wherein in the formula (I) of the linear or branched alkyl group having 1 to 5 carbon atoms represented by $R^1$ to $R^{10}$ is selected from the group consisting of methyl, ethyl, propyl, isopropyl, butyl, secondary butyl, tertiary butyl, isobutyl, pentyl, secondary pentyl, tertiary pentyl, isopentyl and neopentyl.

15. The thin film material according to claim 13, wherein in the formula (I) of the branched alkyl group having 4 to 8 carbon atoms represented by $R^{11}$ is selected from the group consisting of secondary butyl, tertiary butyl, isobutyl, secondary pentyl, tertiary pentyl, isopentyl, neopentyl, isoheptyl, tertiary heptyl, isooctyl, tertiary octyl and 2-ethylhexyl.

16. A thin-film-forming material comprising a molybdenum imide compound represented by the following formula (I), used in a method for producing a thin film, the method comprising:

introducing, onto a substrate, a vapor that has been obtained by vaporizing the thin-film-forming material and that comprises the molybdenum imide compound; and forming a thin film comprising molybdenum on the substrate by decomposing and/or chemically reacting the molybdenum imide compound (1)

wherein $R^1$ through $R^{10}$ each represent a hydrogen atom or a methyl group, and $R^{11}$ is a tertiary pentyl group or a 1,1,3,3-tetramethylbutyl group, and the thin film material is liquid at a temperature lower than 20° C.

\* \* \* \* \*